US00PP21227P3

(12) United States Plant Patent
Dirr

(10) Patent No.: US PP21,227 P3
(45) Date of Patent: Aug. 24, 2010

(54) ***HYDRANGEA ARBORESCENS* PLANT NAMED 'PIIHA-I'**

(50) Latin Name: ***Hydrangea arborescens* L.**
Varietal Denomination: PIIHA-I

(75) Inventor: Michael Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 7 days.

(21) Appl. No.: 12/231,652

(22) Filed: Sep. 4, 2008

(65) Prior Publication Data

US 2010/0058504 P1 Mar. 4, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette H Para
*Assistant Examiner*—Louanne C Krawczewics Myers
(74) *Attorney, Agent, or Firm*—Greenlee Winner and Sullivan PC

(57) ABSTRACT

A new and distinct cultivar of *Hydrangea arborescens* plant named 'PIIHA-I', characterized by its magenta to pink mophead inflorescences; dark green foliage; and upright, spreading growth habit.

3 Drawing Sheets

Genus and species of plant claimed: *Hydrangea arborescens* L.

Variety denomination: 'PIIHA-I'.

BACKGROUND OF THE INVENTION

The present invention relates to a new and distinct cultivar of *Hydrangea arborescens*, a member of the Hydrangeaceae family, hereinafter referred to by its cultivar name 'PIIHA-I'.

This cultivar is grown primarily as an ornamental for landscape use. The cultivar originated as an open-pollinated seedling from a numbered selection, *Hydrangea arborescens* WF-03-03-01-07 (unpatented), in a controlled breeding program to develop a pink mophead *Hydrangea arborescens* in Watkinsville, Ga. WF-03-03-01-07 is a seedling of *Hydrangea arborescens* that was derived by open-pollination from the cultivar 'Wesser Falls' (unpatented).

'PIIHA-I' has been asexually reproduced for multiple generations over the course of two years by softwood cuttings in Watkinsville, Ga. The characteristics of the cultivar have been stable and reproduced true-to-type in successive vegetative generations.

SUMMARY OF THE INVENTION

'PIIHA-I' has not been observed under all possible environmental conditions. The phenotype may vary somewhat with changes in light, temperature, soil and rainfall without, however, any variance in genotype.

The following traits have been repeatedly observed and represent the unique characteristics of the new cultivar. In combination these characteristics distinguish 'PIIHA-I' from all other varieties in commerce known to the inventor. 1) Magenta to pink mophead inflorescences that hold the color for about 5 weeks. 2) Dark green foliage. 3) Upright, spreading growth habit.

'PIIHA-I' is distinguished from its female parent WF-03-03-01-07 by its mophead inflorescence, flower color, and foliage color. The male or pollen parent is unknown, but is one of several *Hydrangea arborescens* in the breeding program, all of which are unpatented. 'PIIHA-I' has magenta to pink mophead inflorescences, whereas WF-03-03-01-07 has pale pink to white lacecap inflorescences. 'PIIHA-I' also has darker green leaves than WF-03-03-01-07.

There are no other pink mophead cultivars of *Hydrangea arborescens* known to the inventor.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Hydrangea*.

DETAILED DESCRIPTION

Figure 1:
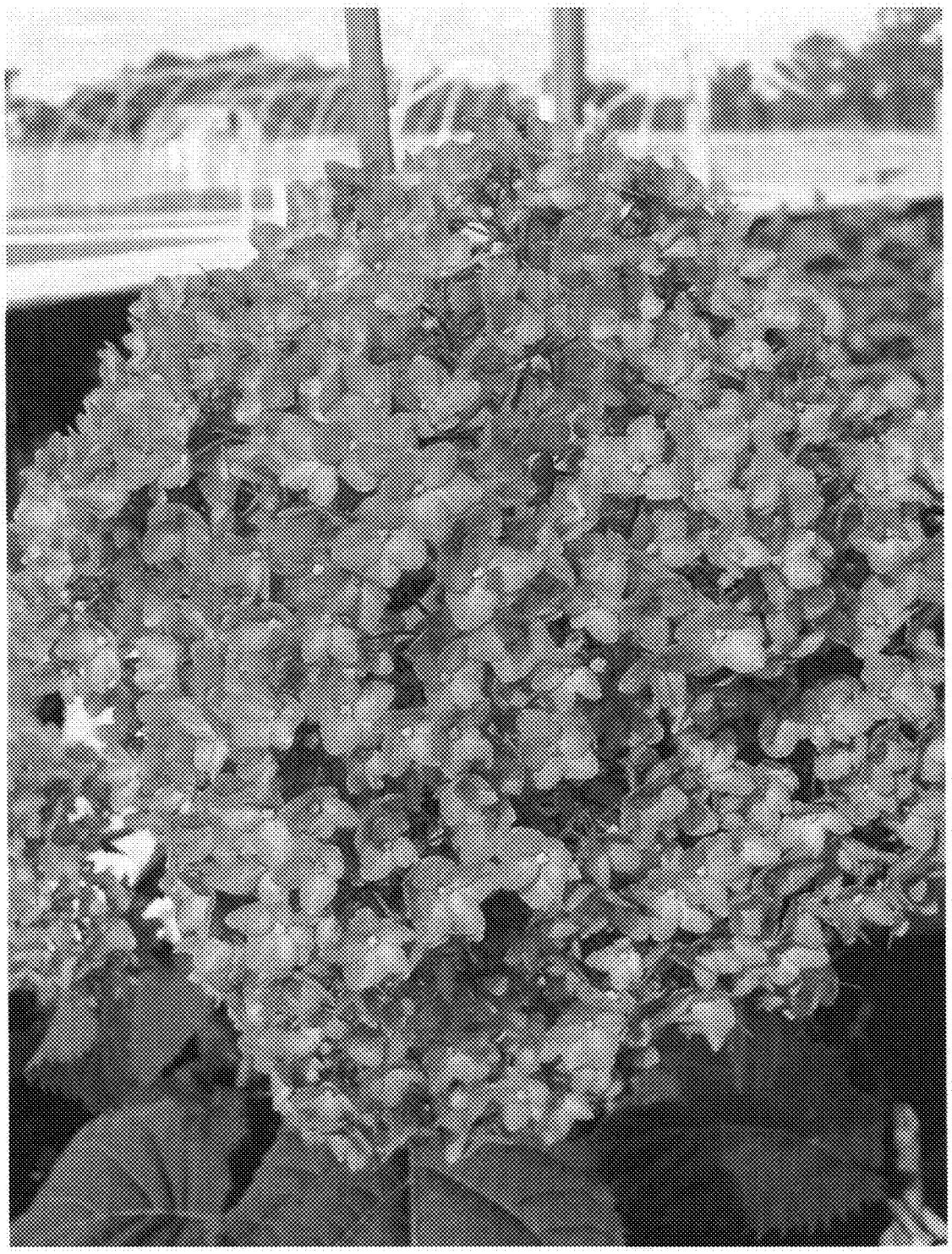
FIG. 1 shows a mature inflorescence on 'PIIHA-I' in summer.
Figure 2:
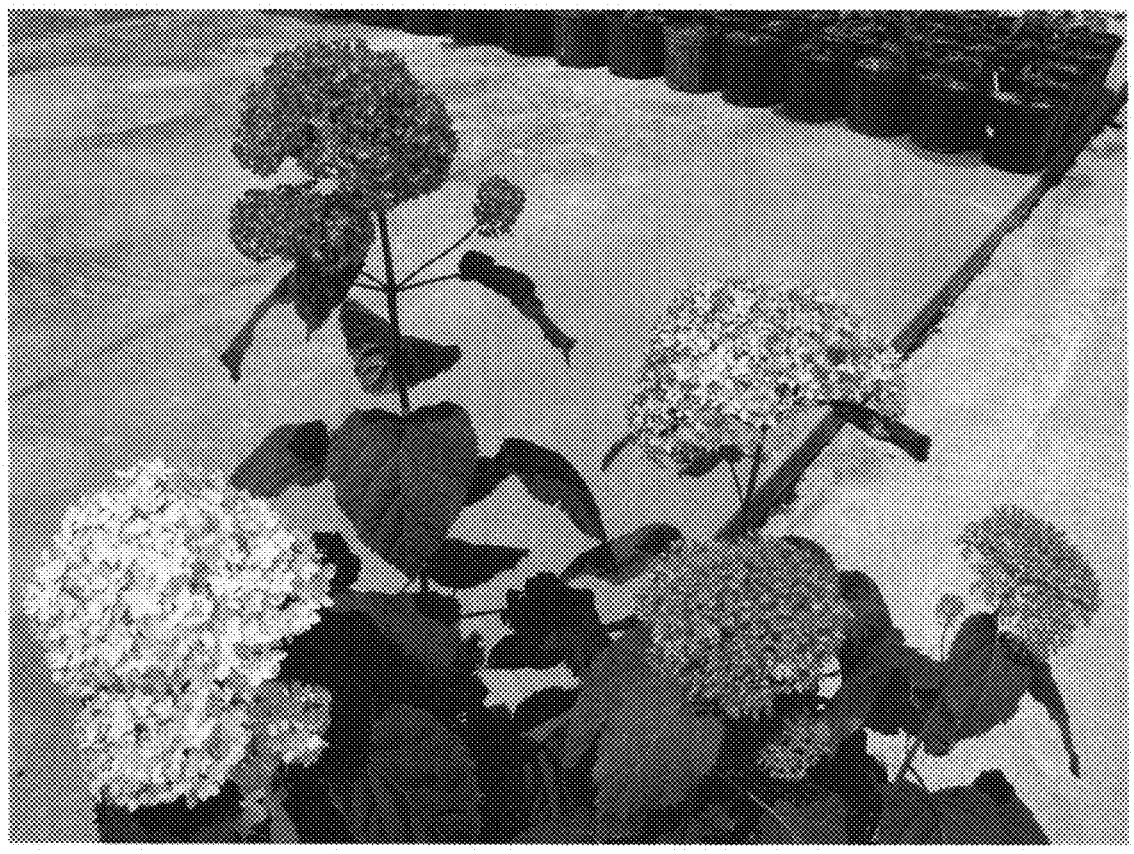
FIG. 2 shows a comparison of 'PIIHA-I' (second from left) to other seedlings from the same open-pollination.
Figure 3:
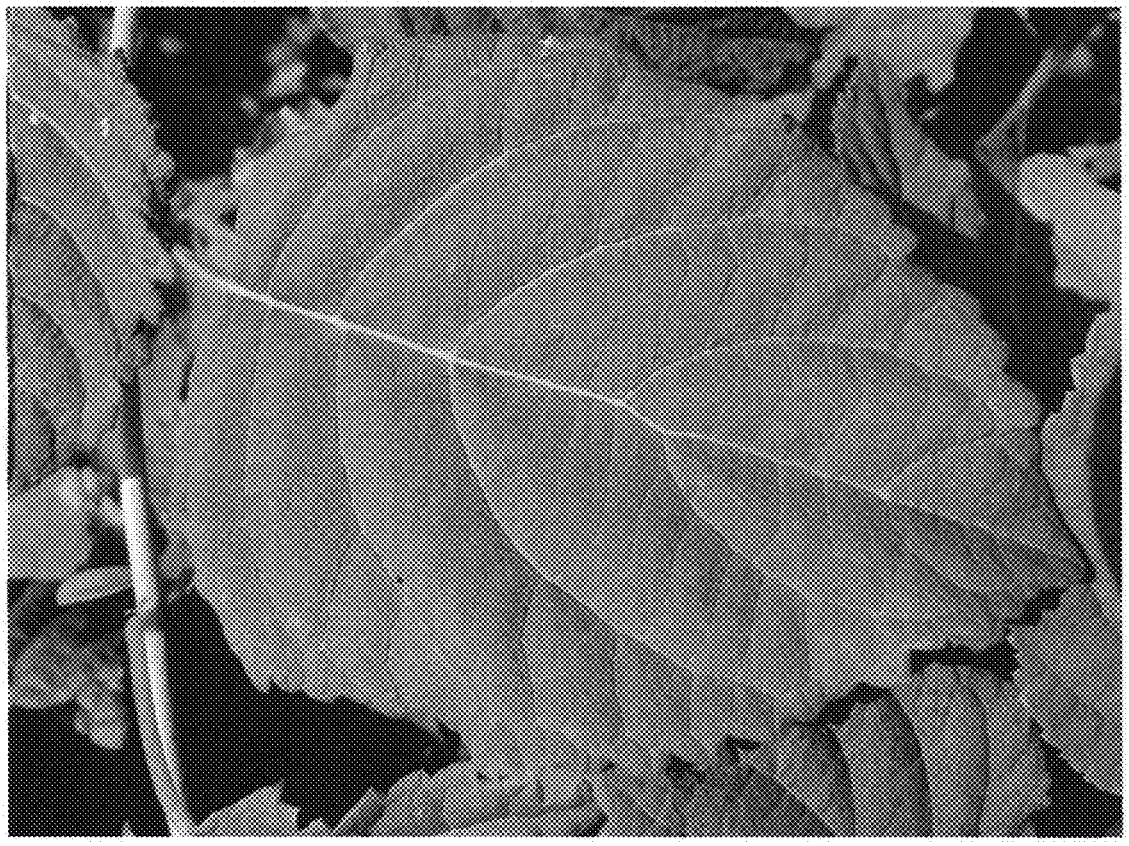
FIG. 3 shows mature foliage in summer on 'PIIHA-I'.

In the following description, color references are made to The Royal Horticultural Society Colour Chart, 2001 Edition, except where general terms of ordinary dictionary significance are used. Plants used for the description and photographs are approximately 2 years old and were grown in 11.8 L containers, with a pH of approximately 6, under 50% shade under outdoor conditions in Watkinsville, Ga. Colors are described using The Royal Horticultural Society (R.H.S.) Colour Chart. Flower color of 'PIIHA-I' is unaffected by pH of the growing media and the availability of aluminum.

Botanical classification: 'PIIHA-I' is a cultivar of *Hydrangea arborescens*.

Parentage: The current variety is an open-pollinated progeny from a numbered selection of *Hydrangea arborescens*, WF-03-03-01-07 (unpatented).

Propagation: Vegetatively by stem cuttings.

Plant description: The claimed variety is an upright, spreading deciduous shrub with a medium to fast growth rate. Freely branching. A saleable plant in an 11.8L container can be produced from a liner in a single season. The plant is hardy in USDA Zones 3 to 9.

*Plant height from the soil level to the top of the inflorescence.*—About 90 cm. Plant diameter: about 90 cm. Side shoots range in length from about 15 to 30 cm.

*Stems.*—First year stems have a diameter of about 7 mm, a round shape. Pubescence: very fine. Stem color: close to 146C with some areas close to 181B. Exfoliation: on first year stems once mature, flaky and stringy. Second year stems have a diameter of about 1 cm and color close to 199B.

*Internode length.*—About 6 cm.

*Vegetative buds.*—Arrangement: opposite. Shape: ovoid. Size: about 3 mm in length and about 1 mm in width. Color: close to 146C.

Foliage description:

*Arrangement.*—Opposite, simple.

*Size.*—About 13.2 cm in length and about 9.6 cm in width.

*Shape.*—Ovate, with acuminate apex, rounded or cordate base, and serrate margin.

*Texture.*—Papery, soft above, rough below.

*Color.*—Emerging leaves are close to 144C on the upper and lower surfaces; mature leaves on the upper surface are close to 147A, and close to 147C on the lower surface. In fall, leaves are 153D and 162A on the upper and lower surfaces.

*Venation.*—Pinnate, veins are impressed into leaves and close to 146C.

*Petiole size and shape.*—About 6.7 cm in length and about 2 mm in diameter, rounded, grooved, glabrous. Petiole color: close to 181A above and 144A below.

Flower description:

*Flower type and arrangement.*—Inflorescence is a corymb (mophead) about 12.5 cm in diameter and about 8 cm high. An inflorescence contains about 300 individual sterile florets and about 75 individual fertile flowers. Inflorescence bloom period: Summer. The sterile flowers retain their color and are effective (showy) for about 5 weeks. The sterile flowers have showy sepals but no petals or reproductive organs. The fertile flowers have petals and reproductive organs but no sepals.

Fertile flowers:

*Flower bud length.*—About 2 mm. Flower bud diameter: about 2 mm. Flower bud shape: round. Color: close to 58A.

*Flower diameter.*—About 7 mm. Flower height: about 5 mm. The fertile flowers within an inflorescence open over a period of one to two weeks and are persistent on the plants.

*Pedicels.*—About 3 mm in length, about 1 mm in width, finely pubescent, and color is close to 181B.

*Petals.*—Fertile flowers have 5 petals per flower and have an effective pollination period of about 2 to 3 days.

*Petal length.*—About 3 mm. Petal width: about 2 mm.

*Petal shape and texture.*—Elliptical, with acute apex, cuneate base, and entire margin. Texture of upper and lower surfaces: smooth with no pubescence.

*Petal color.*—At peak of bloom the upper surface of the petals is close to 58A and the lower surface is close to 63A.

*Stamens.*—Quantity: usually 10 per flower. Anthers: about 1 mm in length and about 1 mm in width, close to 65D. Filaments: about 3 mm in length and about 0.5 mm in width, close to N155B. Pollen: produced in very small quantities per flower (scarce), color close to N155B.

*Pistils.*—Quantity/arrangement: 1 per flower, superior. Pistil length: about 2 mm. Pistil width: about 1 mm. Pistil color: close to N155B. Stigma: usually 2 per pistil, round in shape and close to N155B. Style: about 2 mm in length, tubular in shape, close to N155B. Ovary: 1 per flower, about 1 mm in height and width, and color is close to 143A.

Sterile flowers:

*Flower bud length.*—About 3 mm. Flower bud width: about 2 mm. Flower bud shape: elliptical. Color: close to 58A.

*Flower diameter.*—About 1.5 cm. Flower height: about 1.5 cm. The sterile flowers within an inflorescence open over a period of about one week and are persistent on the plants.

*Pedicels.*—About 1 cm in length, about 1 mm in width, finely pubescent, and color is close to 182A.

*Sepals.*—Sterile flowers contain 3 to 5 (usually 4) sepals per flower.

*Sepal length.*—About 7 mm. Sepal width: about 5 mm.

*Sepal shape and texture.*—Elliptical with acute apex, cuneate base, and entire margin. Texture of upper and lower surfaces: smooth with no pubescence.

*Sepal color.*—Upper surface is close to 58A and the lower surface is close to 63A at peak flowering.

Fruit:

*Type and shape.*—The capsule fruit is ovoid. Length: about 3 mm. Width: about 2 mm. Color: during early ripening is close to 146D and at maturity is close to 200D. Quantity: about 75 per infructescence. Seeds: round, about 0.5 mm in length and about 0.5 mm in width, close to 199B, and each capsule contains about 50 seeds.

Disease/pest resistance: Plants of the claimed *Hydrangea* cultivar grown in the garden have not been noted to be resistant to pathogens and pests common to *Hydrangea*.

I claim:

1. A new and distinct *Hydrangea arborescens* plant named 'PIIHA-I', as illustrated and described herein.

* * * * *